(12) United States Patent
Vitek et al.

(10) Patent No.: US 7,175,596 B2
(45) Date of Patent: Feb. 13, 2007

(54) SYSTEM AND METHOD FOR SENSING AND LOCATING DISTURBANCES IN AN ENERGY PATH OF A FOCUSED ULTRASOUND SYSTEM

(75) Inventors: Shuki Vitek, Haifa (IL); Avner Ezion, Haifa (IL)

(73) Assignee: InSightec-TxSonics Ltd (IL)

( * ) Notice: Subject to any disclaimer, the term of this patent is extended or adjusted under 35 U.S.C. 154(b) by 395 days.

(21) Appl. No.: 10/020,737

(22) Filed: Oct. 29, 2001

(65) Prior Publication Data

US 2003/0083597 A1 May 1, 2003

(51) Int. Cl.
*A61B 8/00* (2006.01)

(52) U.S. Cl. .................. 600/439; 600/437; 601/2; 601/3; 601/4

(58) Field of Classification Search .............. 600/407, 600/411, 425, 427, 437–439; 601/1–5
See application file for complete search history.

(56) References Cited

U.S. PATENT DOCUMENTS

| | | | |
|---|---|---|---|
| 4,865,042 A | 9/1989 | Umemura et al. | |
| 4,873,869 A | 10/1989 | Fink | |
| 4,958,639 A * | 9/1990 | Uchiyama et al. | 600/439 |
| 5,485,839 A * | 1/1996 | Aida et al. | 600/427 |
| 5,520,188 A | 5/1996 | Hennige et al. | |
| 5,526,815 A | 6/1996 | Granz et al. | |
| 5,844,140 A * | 12/1998 | Seale | 73/633 |
| 6,042,556 A * | 3/2000 | Beach et al. | 601/3 |

OTHER PUBLICATIONS

PCT International Search Report for PCT/IB02/05799, Applicant: Insightec-Image Guided Treatment Ltd., Forms PCT/ISA 210, dated Jun. 2, 2003 (4 pages).
PCT Written Opinion of the International Search Authority for PCT/IB02/05799, Applicant: Insightec-Image Guided Treatment Ltd., Form PCT/IPEA/408, dated Jun. 2, 2003 (5 pages).

* cited by examiner

*Primary Examiner*—Brian L. Casler
*Assistant Examiner*—William Jung
(74) *Attorney, Agent, or Firm*—Vista IP Law Group, LLP (57) ABSTRACT

A method for sensing a disturbance in a transmission path of a converging ultrasound energy beam transmitted by a transducer in a focussed ultrasound system comprises transmitting a burst of ultrasound energy from the transducer, detecting whether a reflected portion of the ultrasound energy burst is received at the transducer within a certain time period following transmission of the burst, and, if so, analyzing the received reflected portion to determine a characteristic of the disturbance.

33 Claims, 8 Drawing Sheets

SYSTEM AND METHOD FOR SENSING AND LOCATING DISTURBANCES IN AN ENERGY PATH OF A FOCUSED ULTRASOUND SYSTEM

BACKGROUND OF THE INVENTION

1. Field of the Invention

The invention relates generally to focused ultrasound systems and, more particularly, to systems and methods for sensing and locating discontinuities and disturbances in the energy path of an ultrasound beam in a focused ultrasound system.

2. Background

Thermal energy, such as high intensity focused ultrasonic waves (acoustic waves with a frequency greater than about 20 kilohertz), may be used to therapeutically treat internal tissue regions within a patient. For example, ultrasonic waves may be used to ablate tumors, thereby eliminating the need for invasive surgery. For this purpose, piezoelectric transducers driven by electric signals to produce ultrasonic energy have been suggested that may be placed external to the patient but in close proximity to the tissue to be ablated. The transducer is geometrically shaped and positioned such that the ultrasonic energy is focused in a "focal zone" corresponding to a target tissue region within the patient, heating the target tissue region until the tissue is necrosed. The transducer may be sequentially focused and activated at a number of focal zones in close proximity to one another. This series of "sonications" is used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or sectors, creating a sector-vortex array. The individual transducer elements are driven by radio frequency (RF) electrical signals at the single frequency, but offset in phase and amplitude. In particular, the phase and amplitude of the respective transducer element drive signals may be controlled so as to focus the emitted ultrasonic energy at a desired "focal distance," i.e., the distance from the transducer to the center of the focal zone and provide a desired energy level in the target tissue region.

While the transducer is located external to the patient, it must be in direct contact and tightly coupled with a media that efficiently transmits the high frequency ultrasound waves. For example, the transducer can be positioned in a liquid bath that is capable of efficient transmission of the ultrasound waves. The patient's body must also be wetted and tightly coupled to the transmission media in order to ensure an optimal acoustic wave transmission path from the transducer to the focal zone. If there are any interruptions in continuity (i.e., "discontinuities") along the path, they will generate reflections of the ultrasound waves. Such reflections can reduce the efficiency of the treatment, cause damage to the transducer, and misdirect the ultrasound waves to tissue outside the treatment zone. For example, air pockets or bubbles, can be trapped in the transmission media between the patient and the transducer. Also, the portion of the energy path inside the patient may contain bone or a blood vessel with an air bubble in it, or the sonication process can overheat the targeted tissue causing gas bubbles to form therein.

In other words, it is not uncommon for the transmission path to contain reflective discontinuities or other disturbances. It would be desirable to be able to sense whether any such disturbances in the acoustic energy transmission path exist prior to initiating a sonication, so that corrective action can be taken to avoid harmful reflections of the ultrasound waves.

SUMMARY OF THE INVENTION

According to one aspect of the invention, a method for sensing a disturbance in a transmission path of a converging ultrasound energy beam transmitted by a transducer in a focussed ultrasound system comprises transmitting a burst of ultrasound energy from the transducer and detecting whether a reflected portion of the ultrasound energy burst is received at the transducer within a certain time period following transmission of the burst. If a reflected portion is received at the transducer within a certain time period following transmission of the burst, then one or more characteristics of the received reflected portion (e.g., its intensity or origin) are determined.

Other aspects and features of the invention will become apparent from the following detailed description of preferred embodiments and appended claims, when considered in conjunction with the accompanying drawings.

BRIEF DESCRIPTION OF THE DRAWINGS

Preferred embodiments of the present inventions taught herein are illustrated by way of example, and not by way of limitation, in the Figures of the accompanying drawings, in which.

DETAILED DESCRIPTION OF THE PREFERRED EMBODIMENTS

Figure 1:
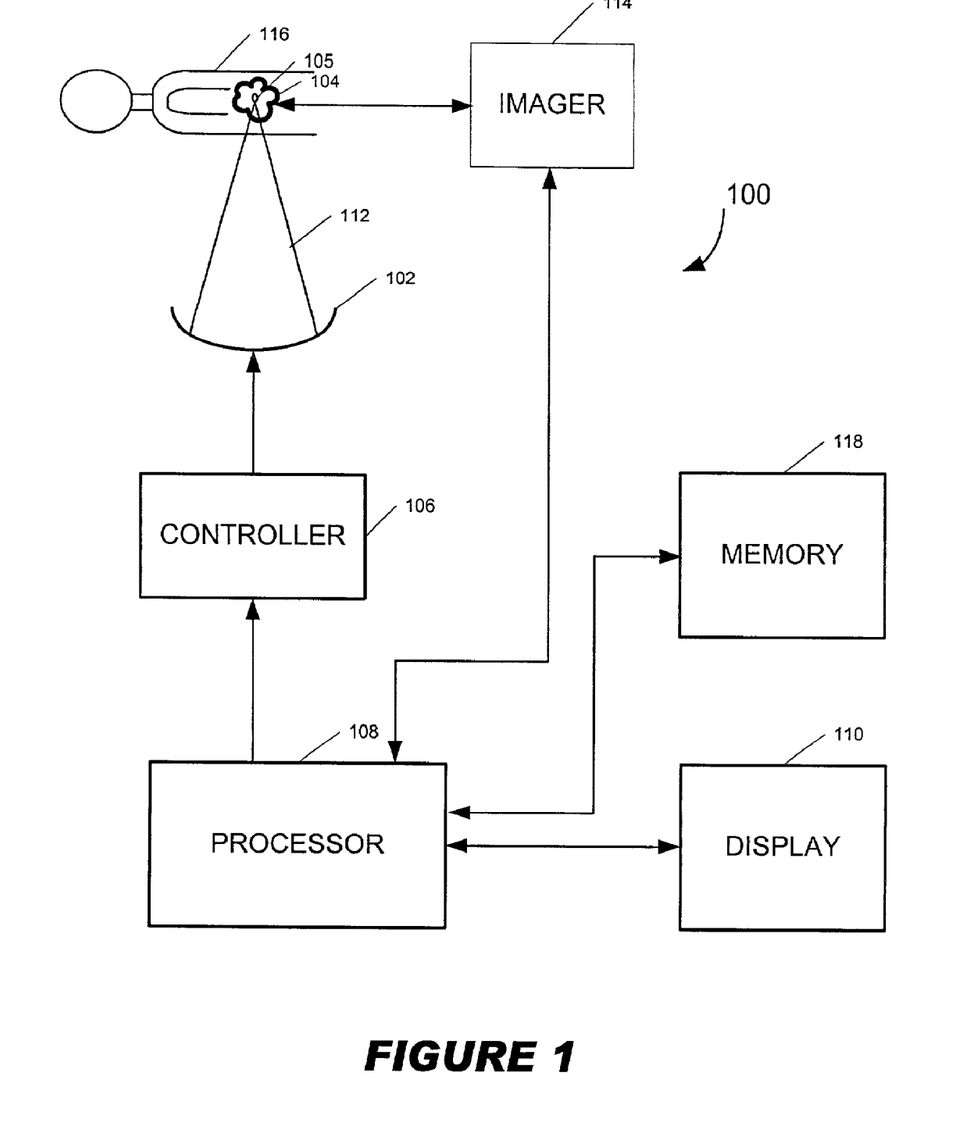
FIG. 1 is a logical block diagram illustrating an example focused ultrasound system in accordance with the invention.

FIG. 1 is a simplified schematic illustration of an exemplary MRI-guided focused ultrasound thermal treatment system 100. The system 100 includes a phased array transducer 102 driven by a controller 106 for emitting a beam of focused ultrasound energy 112, which converges in a focal zone 104 located in a target tissue mass 105 in a patient 116. The actual geometry of the focal zone 104 within the target tissue mass 105 is a function of the shape of the transducer 102 and phasing of the individual transducer elements, which dictate the interaction of the converging ultrasonic waves.

A MRI system 114 is used to acquire images taken along a two-dimensional image plane (or slice) passing through a portion of focal zone 104. The acquired images are processed by a processor 108 to monitor the change in temperature of this portion of tissue mass 105 during a sonication. In particular, the thermal evolution of the focal zone 104 is used to verify that a sufficient tissue "kill" temperature is reached, as well as to track which portions of tissue mass 105 have been killed. This information, in turn, is used by ultrasound controller 106 for positioning ultrasound energy beam 112 (and, thus, focal zone 104) in successive sonications of the tissue mass 105.

More particular aspects, features, embodiments, and preferred systems and methods for operating a MRI-guided focussed ultrasound system are disclosed and described in commonly owned U.S. patent application Ser. Nos. 09/556,095, 09/557,078, 09/724,611, 09/724,670, 09/871,464, and 09/884,206, which are each incorporated by reference herein.

As discussed above, it is important that the transmission path of the ultrasound energy beam 112 from the transducer 102 to the focal zone 104 be free of disturbances that cause reflections of the beam 112 (or a portion thereof). To better illustrate this point, a more detailed view of the ultrasound beam transmission path for system 100 is illustrated in FIG. 2.

Figure 2:
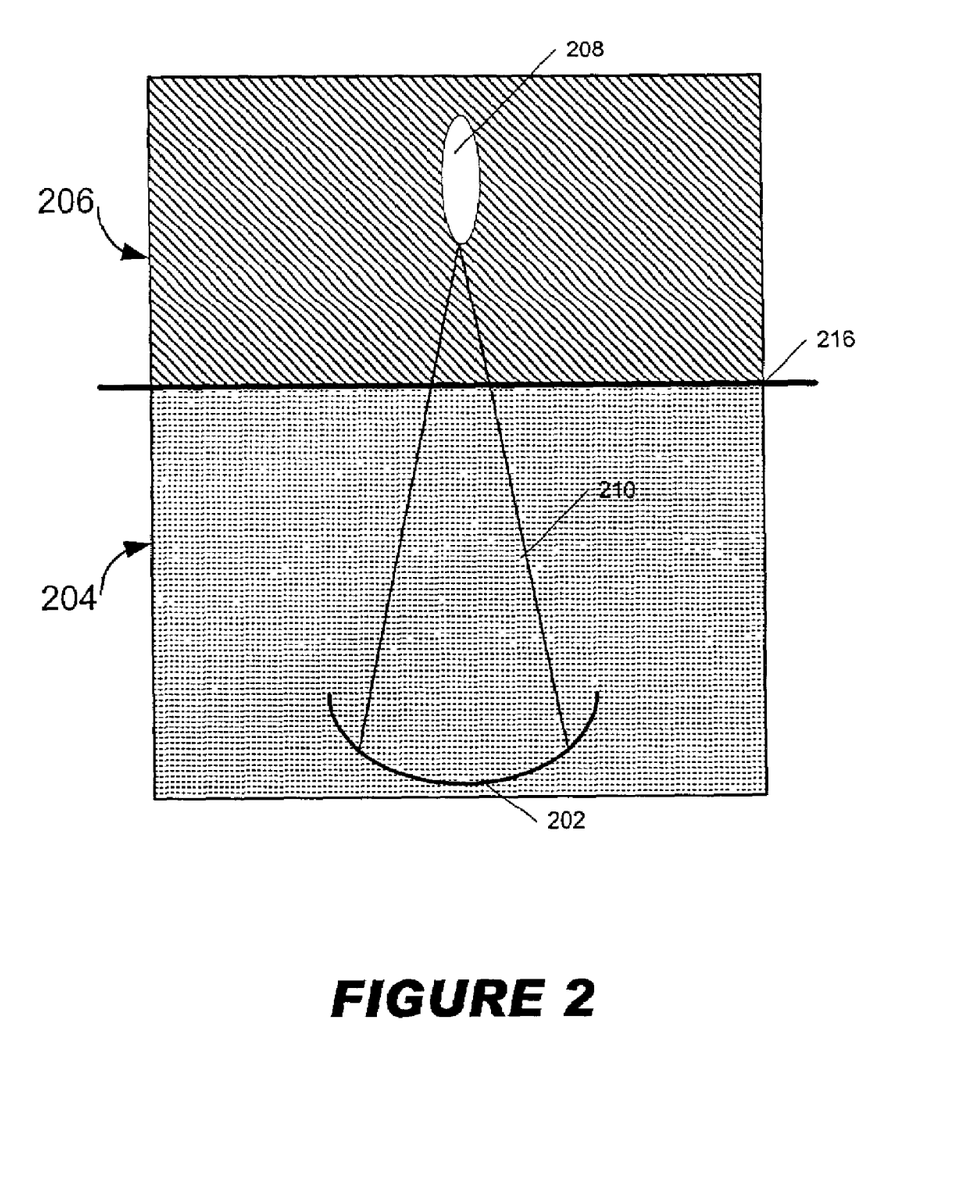
FIG. 2 is a diagram illustrating the transmission path for a focused ultrasound beam produced by the system of FIG. 1.

In FIG. 2, a transducer 202 is located in a bath 204 that is filled with a liquid such as degassed water, which is capable of efficiently transmitting the ultrasound energy beam 210, and sealed with a thin layer of Mylar™. To ensure an efficient transmission path from transducer 202 to a focal zone 208 in a patient 206, a continuous path of liquid(s) separated by non-reflecting mediums must be maintained. Therefore, there must also be a tight coupling between the patient's body and the liquid in bath 204 at boundary 216. Notably, the coupling at boundary 216 can actually comprise multiple layers. For example, the interface between bath 204 and patient 206 preferably comprises a liquid filled cushion, ultrasound jelly, and water. The interface can preferably be adjusted to fit the patient's body structure to ensure a tight coupling and an efficient transmission path.

In general, any break in continuity of the transmission path from transducer 202 to focal zone 104 can generate reflections of ultrasound energy beam 210. Thus, any partial filling of the layers at boundary 216, air bubbles in any one of the layers, or air gaps between the layers can create discontinuities causing reflections of the beam 210. Similarly, partial filling of, or air bubbles in, bath 204 can also cause reflections. The portion of the ultrasound beam transmission path within the body of the patient 206 can also include disturbances that cause reflections. For example, this portion of the transmission path can contain bones or veins or other ducts in the patient's body containing air pockets or bubbles. Thus, disturbances in the transmission path may exist even if the portion of the transmission path between the transducer 202 and the patient's body is free of discontinuities.

Reflections from such discontinuities or disturbances, hereinafter collectively referred to as disturbances, can have multiple negative effects. For example, such reflections can reduce the efficiency of the treatment, cause damage to transducer 202 (i.e., by reflecting the energy in beam 210 back on transducer 202, causing transducer 202 to overheat), or reflect a portion of ultrasound energy beam 210 to tissue outside of the planned treatment zone 208. If energy is reflected to unplanned areas in the vicinity of the patient's body, concentrations of undesired energy next to the skin can result, causing skin burns, or even unintended sonication of the patient's organs.

Figure 3:
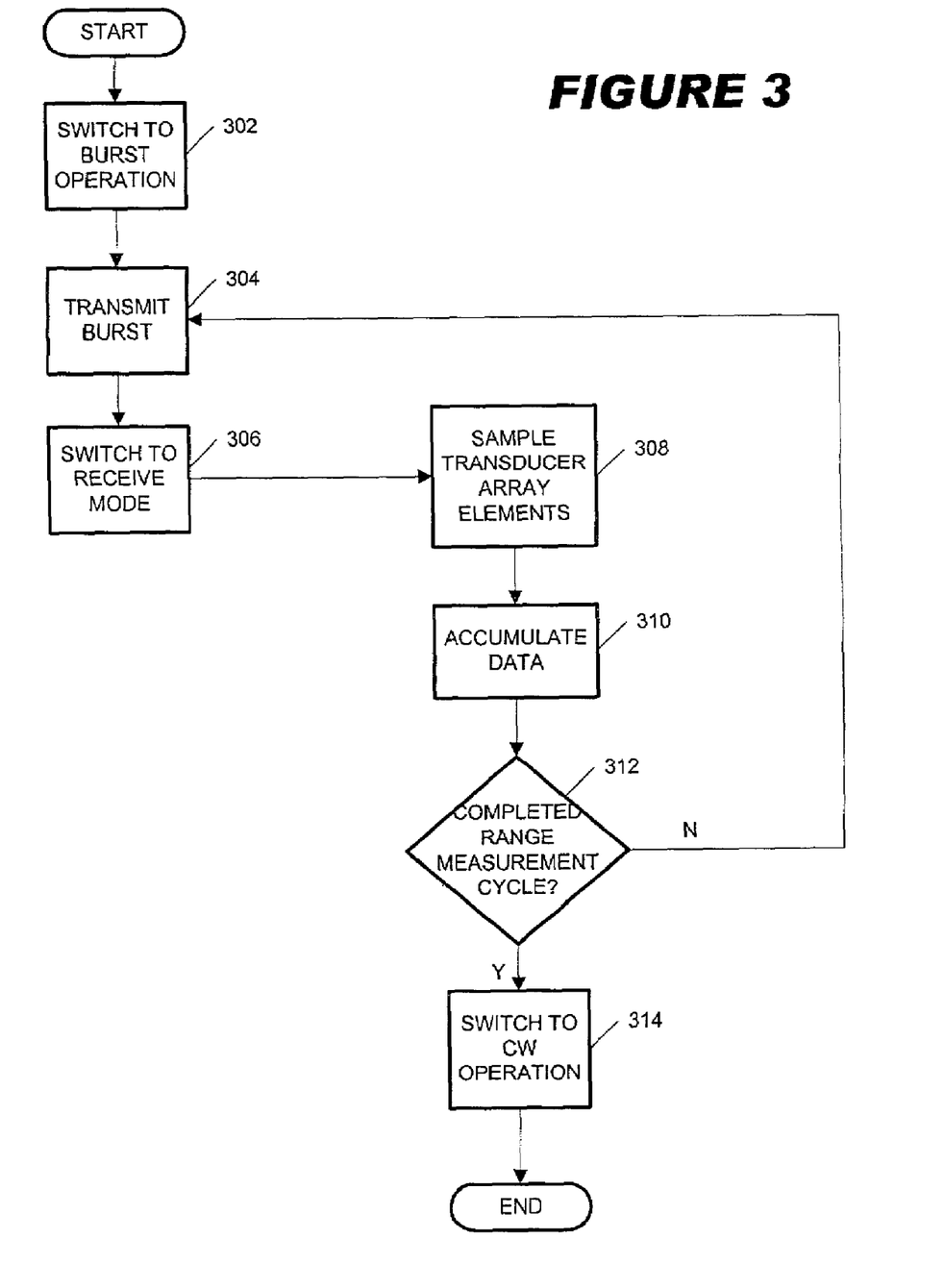
FIG. 3 is a flow chart illustrating an example method for detecting a disturbance in the transmission path of a focused ultrasound beam, in accordance with an embodiment of the invention.

In accordance with one embodiment of the invention, the flow chart of FIG. 3 illustrates an example method for sensing and locating a disturbance in the path of ultrasound energy beam 210, and is now described with reference to focused ultrasound system 100 in FIG. 1.

In step 302, just prior to initiating a sonication, the ultrasound system 100 is switched from a "regular mode" of operation to a "burst mode" of operation in order to sense any disturbances in the acoustic path by sensing delays in echoes of reflected bursts of transmitted energy. Notably, the "regular mode" of operation for system 100 is preferably a continuous, or semi-continuous, wave (CW) mode. A CW mode of operation helps to ensure the most efficient transmission of energy and the shortest possible treatment duration. With "burst mode" operation, on the other hand, a series of narrow bursts of ultrasound energy are transmitted in order to minimize the amount of energy transmitted during the process for sensing and locating any disturbances.

In step 304, a short burst of ultrasound energy is transmitted from transducer 102 in step 304. The burst can, for example, be on the order of twenty micro-seconds long. If transducer 102 comprises an array of transducer elements (which is presumed for the reminder of this detailed description), then the burst transmission preferable involves transmitting a short burst from each transducer array element simultaneously. The burst transmission is preferably focused exactly as planned for the ensuing sonication.

In step 306, immediately following the burst transmission, the system 100 switches transducer 102 from transmit to receive mode, whereby the individual transducer elements comprising the transducer 102 are transformed into individual receivers capable of receiving reflected signals (ultrasound waves) generated by any disturbances in the ultrasound energy transmission path. The reflected signals (if any) received by the transducer elements are sampled (step 308) and preferably digitized and stored (step 310). The duration for which the elements of transducer 102 remain in receive mode in step 306 is preferably at least equal to the time of flight required for the ultrasound waves transmitted in step 304 to travel from the transducer 102, to the focal zone 104, and back to transducer 102; i.e., the maximum roundtrip path for a reflected portion of the burst transmission within the transmission path.

Steps 304, 306, 308 and 310, which are collectively referred to as a "burst transmit-receive cycle," are preferably repeated several times during each disturbance sensing process. Towards this end, in step 312, following each burst transmit-receive cycle, the system 100 determines if another burst transmit-receive cycle is required. If so, then the process reverts back to step 304. If, on the other hand, the disturbance sensing process is complete, and the system 100 switches back to CW operation mode in step 314. In one embodiment, the number of burst transmit-receive cycles for each sensing process is equal to the number of transducer array elements comprising transducer 102. Having the total number of samples equal the total number of transducer elements enables cross correlation of signals from all channels to enhance sensitivity of the detection process and better detect reflections from small disturbances in the wave path.

After the sensed data is accumulated from the respective transducer elements for each burst transmit-receive cycle, it is processed in order to detect the presence of any disturbances in the path of the ultrasound energy beam 112. A main purpose of performing the steps illustrated in FIG. 3 is to determine the range to a reflecting disturbance, as well as the amount of energy reflected by the disturbance (i.e., as measured by the intensity of the reflection).

Figure 4:
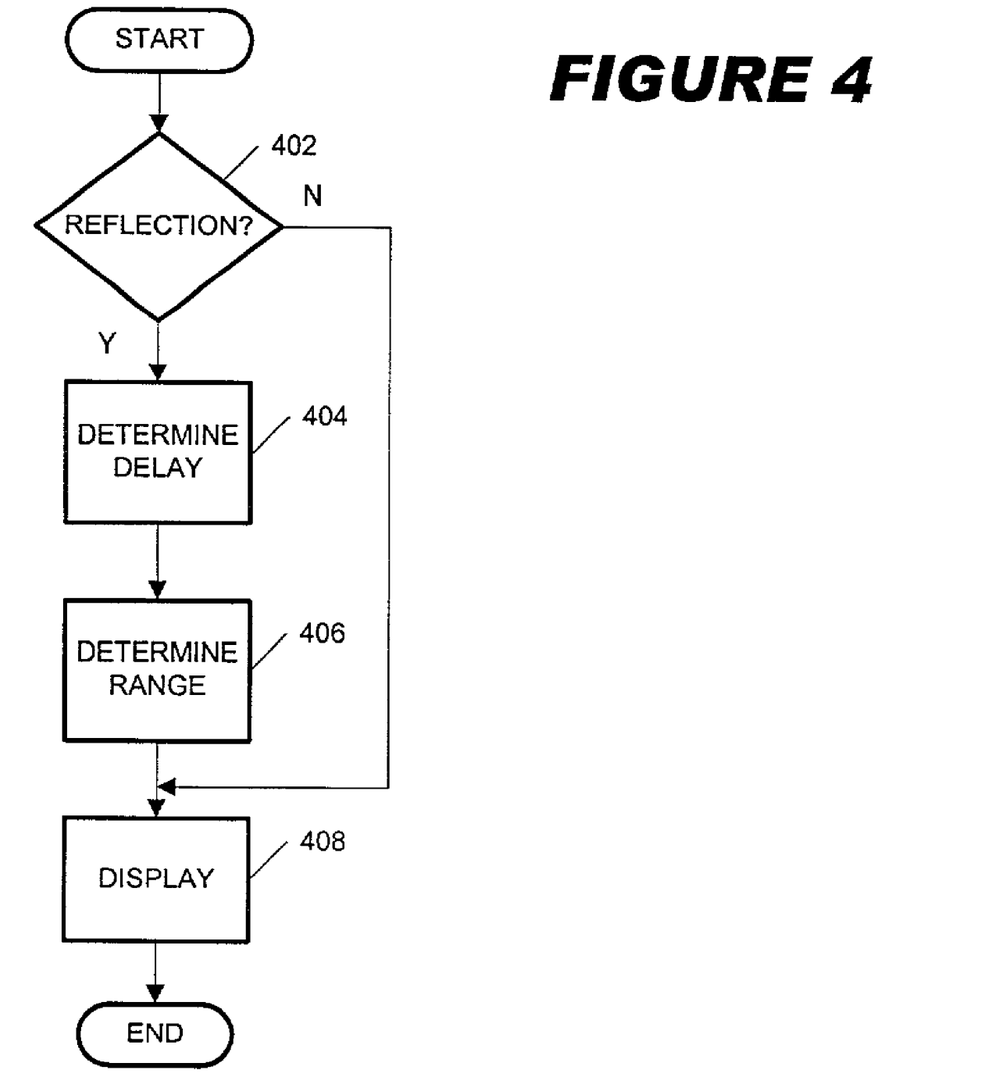
FIG. 4 is a flow chart illustrating an example method for determining the range to a particular disturbance in the transmission path of a focused ultrasound beam, in accordance with an embodiment of the invention.

With this in mind, FIG. 4 is a flow chart illustrating processing of the accumulated sampled data from each burst transmit-receive cycle, in accordance with one embodiment of the invention. First, in step 402, the data is checked to determine if any reflections were received at any of the transducer elements. If a reflection was received at one or more elements, then, in step 404, the reflected energy is analyzed in accordance with a predetermined criteria related to the reflection. For example, the criteria can be the "delay time" from transmission to reception of the reflection. Thus, system 100 can be configured to determine, in step 404, the delay time, which is proportional to the range from the transducer to the disturbance that generated the reflection. In step 406, the range to the disturbance that generated the reflection can then be determined from the delay time, since the speed of sound through the various mediums in the ultrasound beam transmission path are known or may otherwise be sufficiently approximated to accurately determine the range information. Step 404 can also comprise determining the intensity of the reflection. Such information can be used, for example, to determine if system 100 is operating safely.

In step 408, information related to received reflections can be displayed for viewing. As can be seen, even if a reflection is not received from a given burst transmit-receive cycle, it still may be beneficial to display information related to the sampled data, because this information can provide a background or noise level against which a reflection can be compared.

Within system 100, the steps illustrated in the flow charts of FIGS. 3 and 4 can, for example, be performed by a combination of controller 106, processor 108, display 110, and memory 118. Processor 108 preferable controls the operation of system 100 using execution instruction stored in memory 118 in conjunction with any data input from an operator. Such data can, for example, be input through a user interface (not shown), such as a graphical user interface. Thus, processor 108 can include an execution area into which execution instructions are loaded from memory 118. These execution instructions will then cause processor 108 to send commands to controller 106, which controls the operation of transducer 102.

Therefore, processor 108 can be configured to command controller 106 to switch transducer 102 from CW mode operation to burst mode operation. Transducer 102 will then implement steps 304 to 310 for each burst transmit-receive cycle as controlled by controller 106 under the command of processor 108. The sampled data from each step 308 is stored by the processor 108 in the memory 118 at each step 310. The processor 108 uses the stored data to determine the delay (step 404) and the range (step 406).

The processor 108 can include a central processing unit such as a microprocessor or micro controller for executing the instructions stored in memory 118, performing data manipulations, and controlling tasks in system 100. Processor 108 can include one or more additional processors, as well. Such additional processors can include an auxiliary processor to manage input/output, an auxiliary processor to perform floating point mathematical operations, a digital signal processor (DSP) (a special-purpose microprocessor having an architecture suitable for fast execution of signal processing algorithms), a back-end processor (a slave processor subordinate to the main processing system), an additional microprocessor or controller for dual or multiple processor systems, or a coprocessor. These additional processors may be discrete processors or may be built in to the central processing unit.

The processor 108 can be coupled with a communication bus (not shown) that includes a data channel for facilitating information transfer between the processor 108 and the other components of system 100, such as memory 118. The communication bus can also provides a set of signals required for communication with processor 108, including a data bus, address bus, and control bus. Such a communication bus can comprise any known bus architecture according to promulgated standards. These bus architectures include, for example, industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, IEEE P1394, Universal Serial Bus (USB), Access.bus, Apple Desktop Bus (ADB), Concentration Highway Interface (CHI), Fire Wire, Geo Port, or Small Computer Systems Interface (SCSI).

Further, memory 118 can be divided into persistent memory and secondary memory. The persistent memory can be configured to provide storage of instructions, data for programs executing on processor 108, and sampled data from transducer 102. The persistent memory is typically semiconductor-based memory such as programmable read-only memory (PROM), erasable programmable read-only memory (EPROM), electrically erasable read-only memory (EEPROM), or flash memory (block oriented memory similar to EEPROM).

The secondary memory can be configured to provide storage of instructions and data that are loaded into persistent memory or for temporary data used by processor 108. The secondary memory can be static random access memory (SRAM), for example, but any appropriate memory type can be used. Moreover, memory 118 or some portion thereof can comprise a fixed storage drive and/or a removable drive.

Notably, the systems and methods described herein are not limited to the architecture illustrated in FIG. 1. For example, some or all of the controller 106 functionality can be included in processor 108 and vise versa. Thus, the architecture illustrated in FIG. 1 is by way of example only and should not be seen as limiting the invention in any way.

The analysis performed by processor 108 can include determinations of the delay, as mentioned, as well as determinations of the phase and amplitude of reflected signals relative to each transducer array element. This analysis can take into account the coordinates of the focal zone 104 and can produce a variety of data regarding the transmission path for beam 112. For example, the processing performed by processor 108 can allow monitoring and analysis of both the integrative and the individual paths of ultrasound waves transmitted from each transducer array element. By detecting reflections of ultrasound energy beam 112, processor 108 can determine points along the path where disturbances exist in the transmission media, such as air bubbles or a gap in the coupling layers. With this type of analysis, the integrity of the transmission media can be monitored by system 100. This type of analysis can also be used to detect air filed veins or bones in the portion 214 of the transmission path inside the patient's body. Processor 108 can also determine areas of transducer 102 on which high levels of reflected energy are incident. Such analysis in the pre-sonication stage of a treatment can then be used to prevent treatment under conditions that can damage the transducer or result in harm to the patient.

Figure 5:
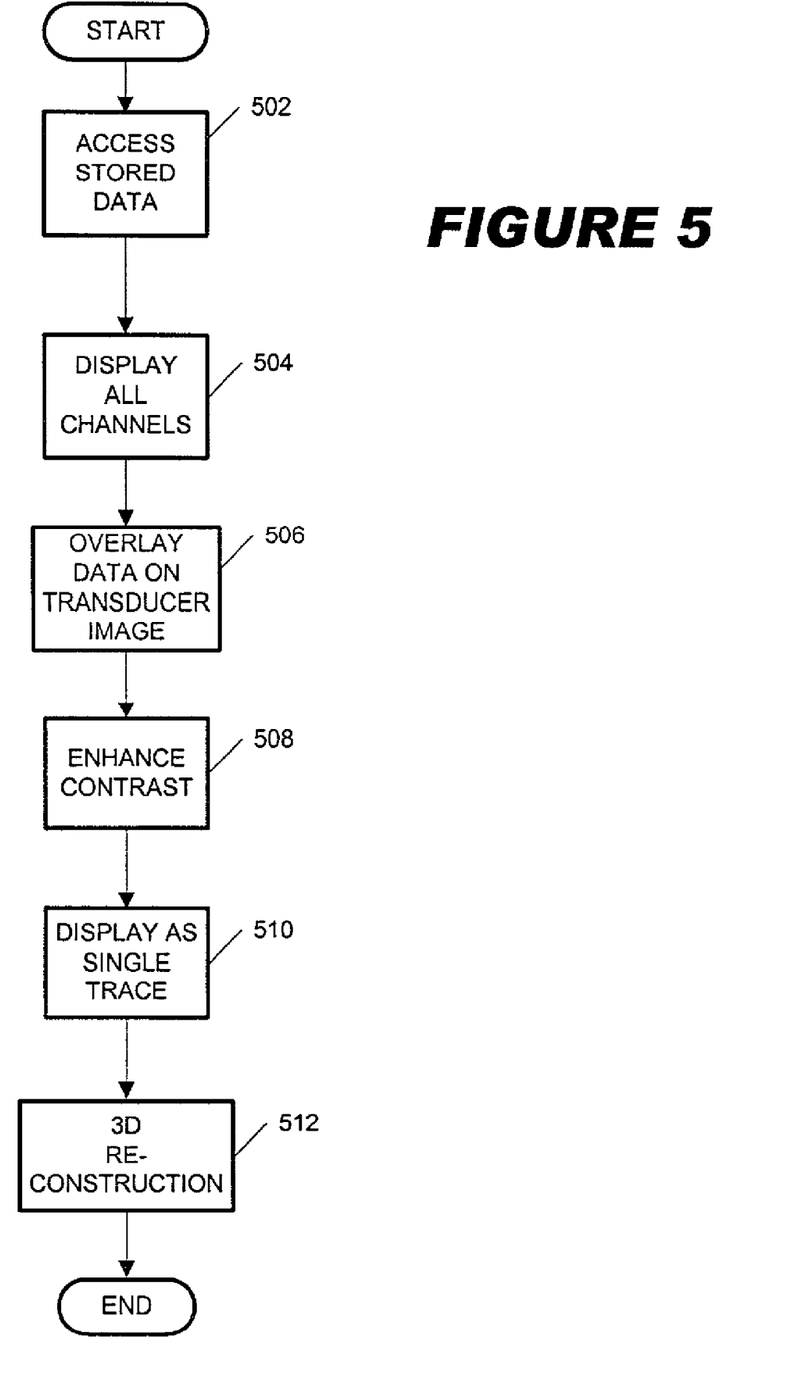
FIG. 5 is a flow chart illustrating a method for processing and displaying data associated with a reflection from a disturbance in the transmission path of a focused ultrasound beam, in accordance with an embodiment of the invention.

The flow chart of FIG. 5 illustrates one embodiment of the invention for processing and displaying the data received by transducer 102, so that the presence of disturbances in the ultrasound beam transmission path can be monitored and visualized. First, in step 502, processor 108 accesses the data stored in memory 118 (step 310). Although, some or all of the processing can be done in real time as the data is received. Next, in step 504, the amplitude of the received signals for each of multiple receive channels is integrated over a certain time period and displayed on display 110.

Figure 6:
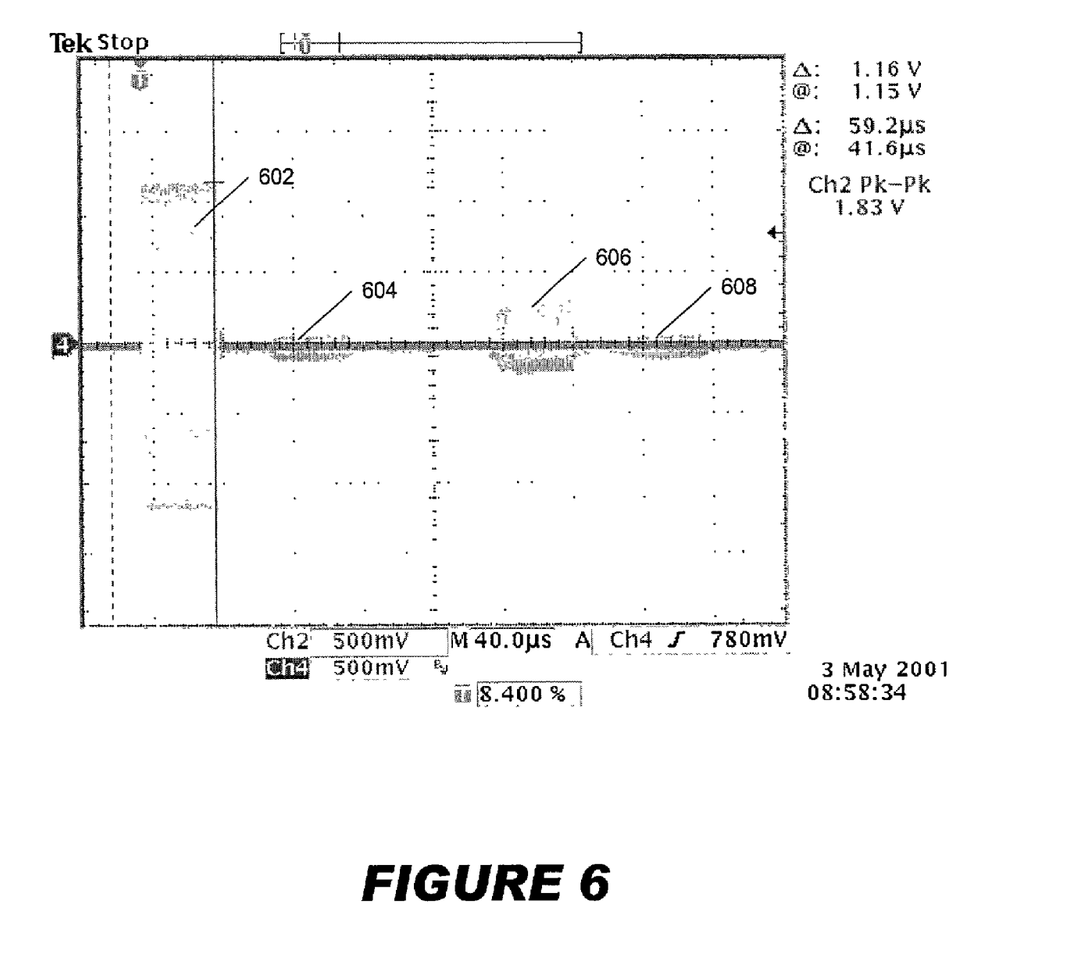
FIG. 6 is a display capture for an oscilloscope that illustrates the reflective signals generated by various disturbances in a transmission path of a focused ultrasound beam.

FIG. 6 illustrates a signal capture of a single receive channel on an oscilloscope. The signals captured in FIG. 6 include a transmitted acoustic signal 602, with a reflected signal waveform, and for purposes of illustration, a reflected waveform from a Mylar™ sheet 604, a reflected signal waveform from a solid barrier 606, and secondary reflections 608. As can be seen in FIG. 6, the captured signals have both positive (upper halo) and negative (lower half) phase components. System 100 preferably comprises multiple receive channels, such as the one illustrated by FIG. 6. For example, system 100 can include a receive channel for each transducer array element or the transducer can be divided into sectors each with a corresponding receive channel.

Thus, in step 504, the received signals for each channel are displayed on display 110. In step 506, the signals for each receive channel can be overlaid and displayed on a representation of the transducer array, which enables visualization of spots where high amounts of reflected energy is incident on the transducer.

Figure 7:
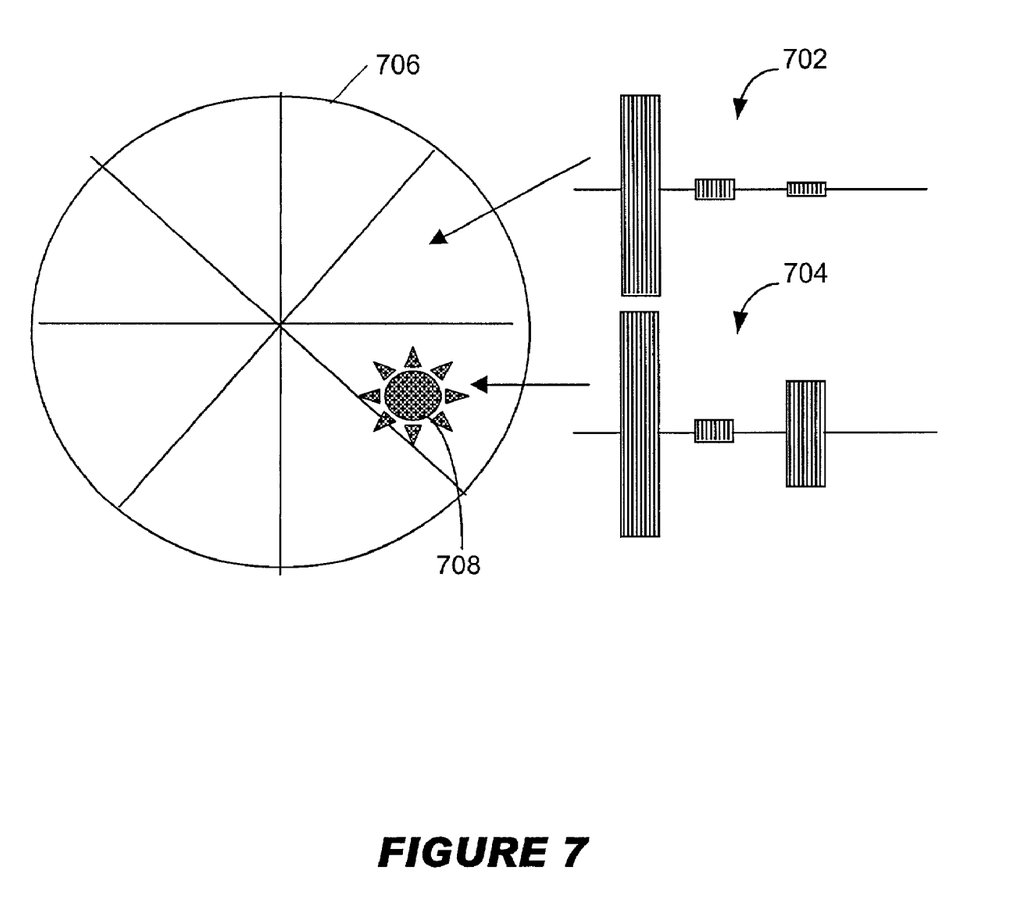
FIG. 7 is a diagram illustrating information related to reflective signals generated by a disturbance in the transmission path of a focused ultrasound beam overlaid on an image of a transducer in order to show the area of the transducer on which the reflective signals are incident.

For example, in FIG. 7, there is a high energy reflection spot 708 on transducer 706. Traces 702 and 704 illustrate the received signal waveforms for a channel corresponding to a transducer sector that does not include reflection spot 708 (channel 702) and for a channel that does include reflection spot 708 (channel 704). As can be seen, trace 704 comprises higher amplitude reflections, indicating the reception of higher amount of reflected energy. The location of reflection spot 708 can then be shown by overlaying traces 702 and 704 on a display of transducer 706.

Enhanced contrast is achieved in step 508 by integrating the absolute value of the amplitudes of the signals received by each channel over specific time slices, which correspond to a restricted window of ranges. In other words, each time slice will correspond to the time it takes acoustic energy beam 112 to travel a certain distance along the transmission path and for any reflected energy to travel back to transducer 102. Thus, the window of possible ranges is bounded at one end by the roundtrip time from transducer 102 to focal spot 104 and back again. At the other end, the window of ranges can be bounded by the time needed for the transducer 102 to be switched to receive mode for receiving any reflections.

Simplistically, two time slices can be selected: one to cover the portion of the transmission path within fluid bath 204; and one to cover the portion of the transmission path within patient 206. All the energy reflected within bath 204 would then be integrated and shown as a composite waveform, as would the reflections generated within patient 206. In practice, however, a finer resolution will likely be needed, which will require the use of many more time slices.

Figure 8A:
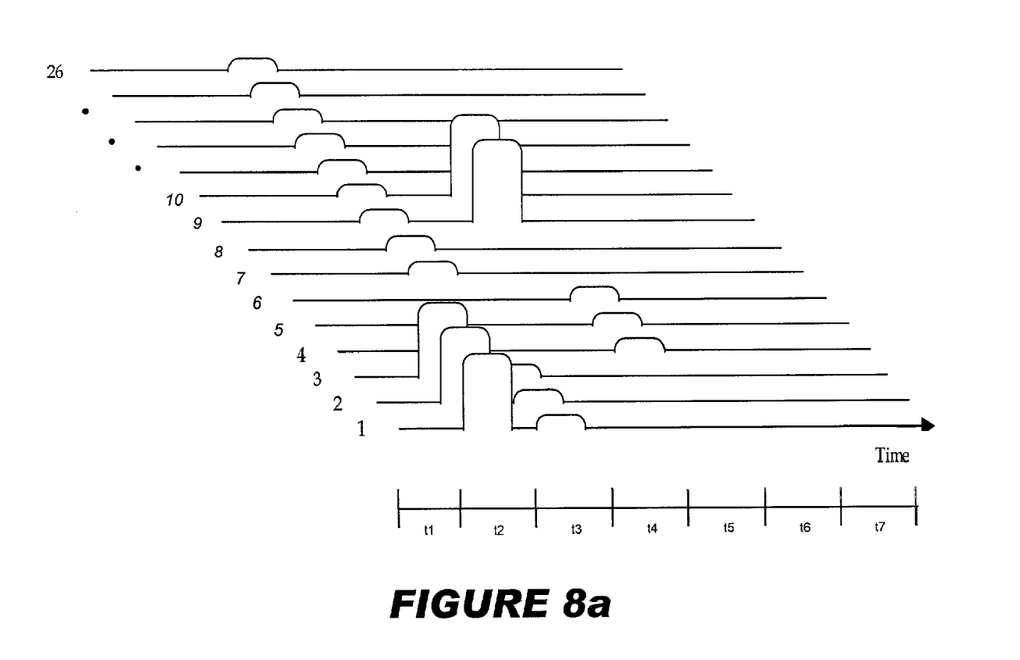
FIG. 8A is a diagram illustrating multiple receive channel traces that show reflective signals generated by one or more disturbances in the transmission path that are received by various transducer array elements.
Figure 8B:
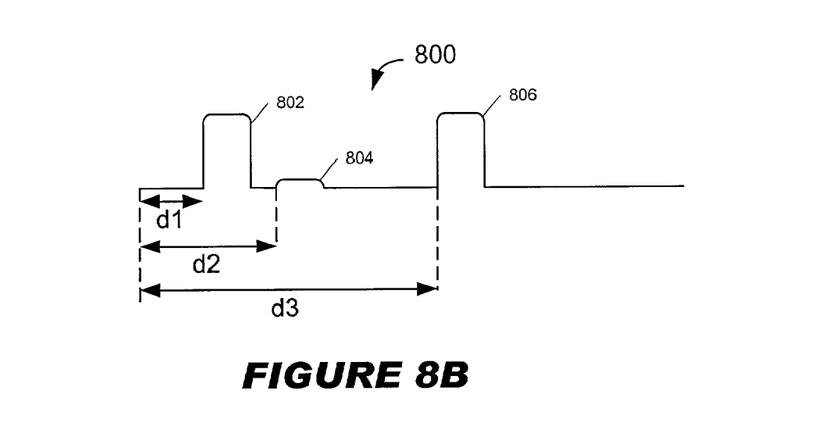
FIG. 8B is a diagram illustrating a single trace comprising composite data from multiple receive channels, such as those illustrated in FIG. 8A.

FIG. 8A illustrates enhanced signal traces for a 26-channel system using time slices t1 to t7. As can be seen, high amounts of reflected energy have been received in various time slices on channels 1–3 and 9 and 10 as well as lesser amounts of energy on various other channels and in various other time slices. Displaying this data as a single trace comprising the data from all channels 1–26 in step 510 is a convenient method for illustrating the ranges to disturbances that even partially reflect acoustic energy beam 112. Such a display is illustrated by trace 800 in FIG. 8B.

The delay determined by processor 108 is the delay from transmission of beam 112 to reception of a reflection waveform. If waveforms 802, 804, and 806 are reflections, for example, then delays d1, d2, and d3 would be the corresponding delays. Delays d1, d2, and d3 can then be turned into a range to the particular disturbance that generated each reflection. Combining the display of FIG. 8B with that of FIG. 7, both the range to a disturbance and the area on which reflected energy therefrom is incident on transducer 706 can be easily visualized by an operator of system 100.

In step 512, a 3D reconstruction of the reflective disturbance can be generated using an advanced method of multiple delay summation. When an ultrasound beam hits a reflective disturbance, energy waves reflect in a multiple directions from each point along the surface of the disturbance. Directional wave vectors can be used to represent these reflective waves travelling in different directions. Reflected waves traveling along different wave vectors will fall incident on different transducer array elements. By summing the data for received reflections along the different vectors, the surface of the particular disturbance at a given point can be recreated. To ensure that only waves reflected from the point of interested are used in the summation, only waves with delay and phase corresponding to reflections from the particular point are collected and used. To create a 3D representation of the reflective surface, the vector data is collected and summed for multiple points, i.e., different delays and phases, along the surface. It should be pointed out that the steps illustrated in FIG. 5 can be carried out in a different order, depending on the implementation. Moreover, some or all of the steps can be omitted as required by the particular implementation.

Thus, the systems and methods for sensing, locating and mapping disturbances in an energy beam of a focused ultrasound system can be used to identify the location and shape of reflective disturbances in the transmission path of a focused ultrasound system. This information can then be used by the treatment system, or an operator thereof, to ensure that an efficient transmission path that is free of reflective disturbances is maintained from a transducer to a focal zone within a patient. This capability can be used to prevent damage to the transducer or to the patient as well as to reduce the time and number of required sanctions.

While embodiments and implementations of the invention have been shown and described, it should be apparent that many more embodiments and implementations are within the scope of the invention. Accordingly, the invention is not to be restricted, except as set forth in the claims and their equivalents.

What is claimed is:

1. A method for sensing a disturbance in a transmission path of a converging ultrasound energy beam transmitted by a transducer in a focused ultrasound system, the method comprising:
   transmitting a burst of ultrasound energy from the transducer, along the transmission path, to a focal zone;
   detecting whether a reflected portion of the ultrasound energy burst is received at the transducer within a certain time period following transmission of the burst, wherein receipt within the time period indicates the reflected portion was reflected by a disturbance located in the transmission path proximal of the focal zone; and
   determining the location of the disturbance based, at least in part, on a delay time from the transmission of the ultrasound energy burst to the reception of the reflected portions of the ultrasound energy bursts from the proximally located disturbance.

2. The method of claim 1, further comprising analyzing the received reflected portion from the disturbance and determining an intensity of the reflected portion.

3. The method of claim 2, further comprising determining at least one or more characteristics of the disturbance based, at least in part, on the determined intensity of the reflected portion.

4. The method of claim 3, further comprising detecting whether a reflected portion of the ultrasound energy burst is received at the transducer comprises sampling each transducer element after simultaneously transmitting a burst of ultrasound energy from each of the transducer elements to determine which, if any, transducer element receives a reflected portion of the burst.

5. The method of claim 4, further comprising repeating each step one or more times.

6. The method of claim 4, further comprising analyzing the received reflected portion from the disturbance and determining a delay time from when the burst was transmitted to when the reflected portion was received at the transducer for each transducer element that receives a reflected portion of the ultrasound energy burst.

7. The method of claim 1, wherein the transducer comprises an array of transducer elements, and wherein transmitting a burst of ultrasound energy from the transducer comprises simultaneously transmitting a burst of ultrasound energy from each of the transducer elements.

8. The method of claim 1, further comprising storing data related to a received reflected portion of the ultrasound energy burst.

9. The method of claim 8, wherein the stored data related to a received reflected portion of the ultrasound energy burst comprises at least one of a group consisting of a determined delay time from when the burst was transmitted to when the received reflected portion was received at the transducer, a determined distance from the transducer to a disturbance reflecting the respective portion back to the transducer, and a determined intensity of the reflected portion.

10. The method of claim 1, further comprising displaying information related to a received reflected portion of the ultrasound energy burst.

11. The method of claim 10, wherein displaying information comprises overlaying data related to a received reflected portion on an image of the transducer in order to indicate a portion of the transducer which received the reflection.

12. The method of claim 11, further comprising displaying the information as a single trace of data.

13. The method of claim 1, further comprising switching a transducer used to transmit the burst of ultrasound energy from continuous wave operation to burst operation before transmitting the burst of ultrasound energy, and thereafter switching the transducer from burst operation to continuous wave operation after a time period required for the burst of ultrasound energy to travel from the transducer to the focal zone and back to the transducer.

14. A focused ultrasound system comprising:
   a transducer configured to transmit a burst of ultrasound energy in a converging transmission path to a focal zone, and to received reflected portions of the ultrasound energy burst,
   the system configured to analyze reflected portions of an ultrasound energy burst received by the transducer within a certain time period following transmission of the respective burst and to determine the location of a disturbance located in the transmission path proximal of the focal zone based, at least in part on a delay time from the transmission of the ultrasound energy burst to the reception of the reflected portions of the ultrasound enemy burst from the disturbance.

15. The focused ultrasound system of claim 14, wherein analysis of the received reflected portion comprises determining a distance from the transducer to the disturbance based, at least in part, on the determined delay time.

16. The focused system of claim 14, wherein analysis of the received reflected portion comprises determining an intensity of the reflected portion from the disturbance.

17. The focused ultrasound system of claim 16, wherein analysis of the received reflected portion comprises determining a characteristic of the disturbance based, at least in part, on the determined intensity of the reflected portion.

18. The focused ultrasound system of claim 14, wherein the transducer comprises an array of transducer elements, and wherein the system is further configured to simultaneously transmit a burst of ultrasound energy from each transducer array element.

19. The focused ultrasound system of claim 18, further configured to sample each of the transducer array elements to determine which if any received a reflection of the ultrasound energy from the disturbance in the path of the ultrasound energy.

20. The focused ultrasound system of claim 19, further configured to transmit a series of ultrasound energy bursts from each transducer array element.

21. The focused ultrasound system of claim 20, further configured to serially sample each of the transducer army elements after each transmission in the series of transmitted ultrasound energy bursts.

22. The focused ultrasound system of claim 19, further configured to determine a delay from transmission of a burst of ultrasound energy to reception of a reflection for each transducer element that receives a reflection.

23. The focused ultrasound system of claim 14, further comprising a memory, wherein the system is configured to store information related to the received reflection in the memory.

24. The focused ultrasound system of claim 14, further comprising a display, and wherein the system is configured to display information related to the received reflection on the display.

25. The focused ultrasound system of claim 24, further configured to display the information related to the received reflection overlaid on an image of the transducer.

26. The focused ultrasound system of claim 24, further configured to display the information related to the received reflection as a single trace.

27. The focused ultrasound system of claim 24, further configured to generate a 3D reconstruction of the disturbance, and to display the 3D reconstruction on the display.

28. The focused ultrasound system of claim 14, further comprising a controller communicatively coupled with the transducer, the controller configured to control the operation of the transducer.

29. The focused ultrasound system or claim 28, wherein the controller is configured to switch the transducer from continuous wave operation to burst operation before the transmitter transmits the burst of ultrasound energy and to switch the transducer back to continuous wave operation after a time period required for the ultrasound energy to travel from the transducer to a focal spot of the transducer and back to the transducer again.

30. The focused ultrasound system of claim 14, further comprising a processor, wherein the processor determines the range from the transducer to the disturbance that generated the reflection.

31. The focused ultrasound system of claim 30, wherein the processor determines the phase and amplitude of the received reflection.

32. The focused ultrasound system of claim 31, wherein the transducer comprises an array of transducer elements, and wherein the processor determines the phase and amplitude of the received reflection relative to each transducer array element.

33. The focused ultrasound system of claim 30, further configured to analyze the integrity of the burst of ultrasound energy transmission path.

* * * * *